(12) United States Patent
Galauner et al.

(10) Patent No.: US 7,494,344 B2
(45) Date of Patent: Feb. 24, 2009

(54) HEATING ELEMENT CONNECTOR ASSEMBLY WITH PRESS-FIT TERMINALS

(75) Inventors: Charles Galauner, Elburn, IL (US); Gregory Menn, Naperville, IL (US); Richard A. Nelson, Geneva, IL (US); Hazelton P. Avery, Batavia, IL (US); Timothy E. Purkis, Naperville, IL (US); Richard A. Faje, Darien, IL (US)

(73) Assignees: Molex Incorporated, Lisle, IL (US); Alexza Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 11/645,916

(22) Filed: Dec. 27, 2006

(65) Prior Publication Data

US 2007/0155255 A1 Jul. 5, 2007

Related U.S. Application Data

(60) Provisional application No. 60/754,715, filed on Dec. 29, 2005.

(51) Int. Cl.
*H01R 9/09* (2006.01)
(52) U.S. Cl. ........................................ 439/67
(58) Field of Classification Search ................. 739/75, 739/845, 891, 83; 219/213, 528, 537, 532, 219/215; 392/470, 451, 434, 435; 361/823; 439/891, 67, 567, 493, 496, 75, 571, 508; 335/51; 174/35 C; 403/408.1; 411/508; 128/203.27; 99/326
See application file for complete search history.

(56) References Cited

U.S. PATENT DOCUMENTS

| | | | | |
|---|---|---|---|---|
| 3,342,977 A | * | 9/1967 | Anderson | .................. 219/548 |
| 3,417,680 A | * | 12/1968 | Crone et al. | .................. 404/89 |
| 3,575,678 A | * | 4/1971 | Barton | ........................ 335/151 |
| 4,097,113 A | | 6/1978 | McKelvy | |
| 4,100,395 A | * | 7/1978 | Ballard | ........................ 392/434 |
| 4,262,190 A | * | 4/1981 | Hager, Jr. | .................... 392/433 |
| 4,322,605 A | * | 3/1982 | Stimens | ....................... 219/532 |
| 4,450,343 A | * | 5/1984 | Dundon | ....................... 392/434 |
| 4,551,614 A | * | 11/1985 | Johnson | ....................... 392/433 |
| 4,588,976 A | * | 5/1986 | Jaselli | ........................ 338/284 |

(Continued)

FOREIGN PATENT DOCUMENTS

DE 2449739 4/1976

(Continued)

OTHER PUBLICATIONS

International Search Report of the International Application No. PCT/US2006/049363.

*Primary Examiner*—Alexander Gilman
(74) *Attorney, Agent, or Firm*—Thomas D. Paulius

(57) ABSTRACT

An improved heating element connector assembly includes an insulative, rectangular frame with a central opening and a plurality of conductive terminals which are press fit into openings in the frame. The terminals are spaced apart from each other lengthwise of two opposing sidewalls of the frame, and pairs of terminals are aligned with each other between the two sidewalls. A plurality of conductive strips extend across the frame opening to interconnect the pairs of terminals together. The terminals include compliant pin tail portions for receipt by corresponding holes formed in a circuit board of the assembly and deformable head portions for crimping onto the conductive strips.

21 Claims, 7 Drawing Sheets

U.S. PATENT DOCUMENTS

| | | | |
|---|---|---|---|
| 4,598,206 A * | 7/1986 | Nelson | 250/495.1 |
| 4,735,217 A | 4/1988 | Gerth et al. | |
| 4,781,607 A * | 11/1988 | Rumbaugh | 439/191 |
| 4,819,665 A | 4/1989 | Roberts et al. | |
| 4,889,999 A * | 12/1989 | Rowen | 307/31 |
| 4,892,109 A | 1/1990 | Strubel | |
| 4,894,015 A | 1/1990 | Stockero et al. | |
| 4,917,119 A | 4/1990 | Potter et al. | |
| 4,922,901 A | 5/1990 | Brooks et al. | |
| 4,935,624 A | 6/1990 | Henion et al. | |
| 4,941,483 A | 7/1990 | Ridings et al. | |
| 4,947,874 A | 8/1990 | Brooks et al. | |
| 4,947,875 A | 8/1990 | Brooks et al. | |
| 4,968,885 A | 11/1990 | Willoughby | |
| 5,038,769 A | 8/1991 | Krauser | |
| 5,060,671 A | 10/1991 | Counts et al. | |
| 5,093,894 A | 3/1992 | Deevi et al. | |
| 5,095,921 A | 3/1992 | Losee et al. | |
| 5,099,861 A | 3/1992 | Clearman et al. | |
| 5,135,009 A | 8/1992 | Muller et al. | |
| 5,144,962 A | 9/1992 | Counts et al. | |
| 5,179,966 A | 1/1993 | Losee et al. | |
| 5,181,854 A * | 1/1993 | Masuda | 439/67 |
| 5,224,498 A | 7/1993 | Deevi et al. | |
| 5,226,411 A | 7/1993 | Levine | |
| 5,269,327 A | 12/1993 | Counts et al. | |
| 5,285,798 A | 2/1994 | Banerjee et al. | |
| 5,286,218 A | 2/1994 | Sakurai | |
| 5,322,075 A | 6/1994 | Deevi et al. | |
| 5,357,984 A | 10/1994 | Farrier et al. | |
| 5,400,969 A | 3/1995 | Keene | |
| 5,402,517 A | 3/1995 | Gillett et al. | |
| 5,408,574 A | 4/1995 | Deevi et al. | |
| 5,456,247 A | 10/1995 | Shilling et al. | |
| 5,479,948 A | 1/1996 | Counts et al. | |
| 5,505,214 A | 4/1996 | Collins et al. | |
| 5,537,507 A | 7/1996 | Mariner et al. | |
| 5,538,020 A | 7/1996 | Farrier et al. | |
| 5,565,148 A | 10/1996 | Pendergrass | |
| 5,577,156 A | 11/1996 | Costello | |
| 5,591,409 A | 1/1997 | Watkins | |
| 5,593,792 A | 1/1997 | Farrier et al. | |
| 5,613,504 A | 3/1997 | Collins et al. | |
| 5,613,505 A | 3/1997 | Campbell et al. | |
| 5,666,977 A | 9/1997 | Higgins et al. | |
| 5,735,263 A | 4/1998 | Rubsamen et al. | |
| 5,808,279 A * | 9/1998 | De Nichilo | 219/537 |
| 5,819,756 A | 10/1998 | Mielordt | |
| 5,824,996 A * | 10/1998 | Kochman et al. | 219/529 |
| 5,865,185 A | 2/1999 | Collins et al. | |
| 5,904,900 A | 5/1999 | Bleuse et al. | |
| 5,917,149 A * | 6/1999 | Barcley et al. | 174/378 |
| 5,947,764 A * | 9/1999 | Pan et al. | 439/492 |
| 6,004,516 A | 12/1999 | Rasouli et al. | |
| 6,053,176 A | 4/2000 | Adams et al. | |
| 6,085,026 A | 7/2000 | Hammons et al. | |
| 6,095,153 A | 8/2000 | Kessler et al. | |
| 6,102,036 A | 8/2000 | Slutsky et al. | |
| 6,131,570 A | 10/2000 | Schuster et al. | |
| 6,155,268 A | 12/2000 | Takeuchi | |
| 6,158,431 A | 12/2000 | Poole | |
| 6,178,969 B1 | 1/2001 | St. Charles | |
| 6,206,735 B1 | 3/2001 | Zanolli | |
| 6,234,167 B1 | 5/2001 | Cox et al. | |
| 6,250,301 B1 | 6/2001 | Pate | |
| 6,263,872 B1 | 7/2001 | Schuster et al. | |
| 6,287,156 B1 * | 9/2001 | Swan et al. | 439/845 |
| 6,302,705 B1 * | 10/2001 | Yatskov et al. | 439/67 |
| 6,309,986 B1 | 10/2001 | Flashinski et al. | |
| 6,312,296 B1 | 11/2001 | Jones | |
| 6,319,025 B1 * | 11/2001 | Sudo | 439/83 |
| 6,325,475 B1 | 12/2001 | Hayes et al. | |
| 6,328,033 B1 | 12/2001 | Avrahami | |
| 6,390,453 B1 | 5/2002 | Frederickson et al. | |
| 6,491,233 B2 | 12/2002 | Nichols | |
| 6,501,052 B2 | 12/2002 | Cox et al. | |
| 6,516,796 B1 | 2/2003 | Cox et al. | |
| 6,526,969 B2 | 3/2003 | Nilsson et al. | |
| 6,547,607 B2 | 4/2003 | Moll et al. | |
| 6,557,552 B1 | 5/2003 | Cox et al. | |
| 6,561,186 B2 | 5/2003 | Casper et al. | |
| 6,568,390 B2 | 5/2003 | Nichols et al. | |
| 6,648,950 B2 | 11/2003 | Lee et al. | |
| 6,671,945 B2 | 1/2004 | Gerber et al. | |
| 6,680,668 B2 | 1/2004 | Gerber et al. | |
| 6,681,769 B2 | 1/2004 | Sprinkel et al. | |
| 6,681,998 B2 | 1/2004 | Sharpe et al. | |
| 6,684,880 B2 | 2/2004 | Trueba et al. | |
| 6,688,313 B2 | 2/2004 | Wrenn et al. | |
| 6,694,975 B2 | 2/2004 | Schuster et al. | |
| 6,701,921 B2 | 3/2004 | Sprinkel et al. | |
| 6,701,922 B2 | 3/2004 | Hindle et al. | |
| 6,715,487 B2 | 4/2004 | Nichols et al. | |
| 6,728,478 B2 | 4/2004 | Cox et al. | |
| 6,984,796 B2 * | 1/2006 | Blossfeld | 200/284 |
| 7,179,091 B2 * | 2/2007 | Mongold | 439/67 |
| 2001/0042546 A1 | 11/2001 | Umeda et al. | |
| 2002/0078955 A1 | 6/2002 | Nichols et al. | |
| 2002/0097139 A1 | 7/2002 | Gerber et al. | |
| 2002/0117175 A1 | 8/2002 | Kottayil et al. | |
| 2003/0015196 A1 | 1/2003 | Hodges et al. | |
| 2003/0015197 A1 | 1/2003 | Hale et al. | |
| 2003/0033055 A1 | 2/2003 | McRae et al. | |
| 2003/0049025 A1 | 3/2003 | Neumann et al. | |
| 2003/0051728 A1 | 3/2003 | Lloyd et al. | |
| 2003/0062042 A1 | 4/2003 | Wensley et al. | |
| 2003/0106551 A1 | 6/2003 | Sprinkel et al. | |
| 2003/0121906 A1 | 7/2003 | Abbott et al. | |
| 2003/0132219 A1 | 7/2003 | Cox et al. | |
| 2003/0156829 A1 | 8/2003 | Cox et al. | |
| 2003/0209240 A1 | 11/2003 | Hale et al. | |
| 2004/0035409 A1 | 2/2004 | Harwig et al. | |
| 2004/0055504 A1 | 3/2004 | Lee et al. | |
| 2004/0081624 A1 | 4/2004 | Nguyen et al. | |
| 2004/0099266 A1 | 5/2004 | Cross et al. | |
| 2005/0268911 A1 | 12/2005 | Cross et al. | |

FOREIGN PATENT DOCUMENTS

| | | |
|---|---|---|
| DE | 3245746 | 6/1984 |
| DE | 10100189 | 7/2001 |
| DE | 10321184 | 12/2004 |
| GB | 732905 | 6/1955 |
| GB | 1567523 | 5/1980 |
| WO | 94/09842 A1 | 5/1994 |
| WO | 02/051466 A2 | 7/2002 |
| WO | 02/051469 A2 | 7/2002 |
| WO | 02/098496 A1 | 12/2002 |
| WO | 03/037412 A2 | 5/2003 |
| WO | 03/049535 A1 | 6/2003 |

* cited by examiner

HEATING ELEMENT CONNECTOR ASSEMBLY WITH PRESS-FIT TERMINALS

REFERENCE TO RELATED APPLICATIONS

This application claims priority from U.S. Provisional Patent Application Ser. No. 60/754,715, filed Dec. 29, 2005, which is hereby incorporated herein by reference.

BACKGROUND OF THE INVENTION

The present invention relates generally to connectors, and more particularly to connector assemblies used in heating assemblies.

Heating elements are used in a variety of applications. Recently, heating elements have been used in drug delivery systems. In such systems, a heating element is provided as an assembly that has a plurality of individual conductive members held upon a frame. The individual elements are coated with a drug, so that when the elements are energized and heated to a specific temperature, the drug is vaporized and a patient can readily and easily inhale the drug.

Current heating element assemblies use a frame and a series of conductive terminals that are mounted to a circuit board. Conductive foil strips are soldered to the circuit board and the foil to create electrical continuity. This manner of construction is expensive and difficult.

Accordingly, the present invention is directed to a heating element connector structure of simplified and reliable construction that has a low cost of manufacture.

SUMMARY OF THE INVENTION

Accordingly, it is a general object or aspect of the present invention to provide a new and improved heating element connector assembly of simplified construction and reduced cost.

It is another object or aspect of the present invention to provide a reliable electrical contact structure for use in a heating element assembly that utilizes only mechanical connections rather than soldered connections and in which the mechanical connections serve to connect together individual conductive strips to conductive terminals.

Yet another object or aspect of the present invention is to provide an improved heating element connector assembly including an insulative, rectangular frame with a central opening, a plurality of conductive terminals disposed in the frame, the terminal being spaced apart from each other lengthwise of two opposing sidewalls of the frame, the terminal further being aligned with each other as between the two sidewalls, and a plurality of conductive strips extending across the frame opening and interconnecting pairs of terminals together, the terminals including compliant pin tail portions for receipt by corresponding holes form in a circuit board associated with the assembly.

Yet a still further object or aspect of an embodiment of the present invention is to provide a heating element connector assembly of the type described above, wherein the terminals include contact portions in the form of posts that can be deformed, as be mushrooming or deadheading into a flattened state in order to connect the conductive strip to the terminal.

In accordance with the present invention, an insulative frame is provided in the form of an open rectangle. The frame has two side walls that are interconnected by a pair of end walls, the end walls preferably being of a shorter length than the side walls to give the frame a rectangular configuration. The frame side walls have a plurality of terminal-receiving cavities disposed in them. These cavities are arranged in an array that runs lengthwise of each frame side wall, and each such cavity receives only a single terminal. The terminals are further aligned together across the frame opening in pairs of terminals.

The assembly also includes a plurality of conductive strips that extend across the frame opening and which interconnect aligned pairs of the terminals together. These conductive strips are preferably formed from a conductive foil, and the foil is further preferably formed with an upward bow in it so that the central portions of the strips rise to a level above the top of the frame.

The terminals are of a press fit style and include a body portion that interconnects a contact portion to a tail portion. The tail portion, in the illustrated embodiment of the invention, takes the form of compliant pins so that the assembly and its terminals may be easily and reliably mounted to a supporting circuit board. The circuit board will have heating circuits disposed thereon which are connected to the terminals so that current may be passed through the strips. The strips are coated with a drug which is vaporized when the strips are energized.

The terminals further have contact portions that rise up from the body portions. The contact portions are best described as deformable lugs, and to facilitate their deforming, the lugs may include center notches. A deforming tool may be used with a center punch or the like to contact the lug and deform it so that, in the illustrated embodiment, the lug preferably deforms within the plane of the terminal body portion. The terminal-receiving cavities are formed with inner steps that act as stop surfaces and which engage corresponding shoulders that are formed on the terminal body portions. These shoulders extend outwardly sideways from the body portions.

The terminal body portions have flat opposing ends. The bottom ends form surfaces that may be used to insert the terminals into their receiving cavities and the top ends form reaction surfaces against which the aforementioned punch may contact or deform the contact portions.

These and other objects, aspects, embodiments, features and advantages of the present invention will be clearly understood through a consideration of the following detailed description. It will be understood that the embodiments described are illustrative of some of the applications of the principles of the present invention. Modifications may be made without departing from the sprit and scope of the invention, including those combinations of features that are individually disclosed or claimed herein.

BRIEF DESCRIPTION OF THE DRAWINGS

In the course of this detailed description, the reference will be frequently made to the attached drawings in which.

DETAILED DESCRIPTION OF THE PREFERRED EMBODIMENTS

Figure 1:
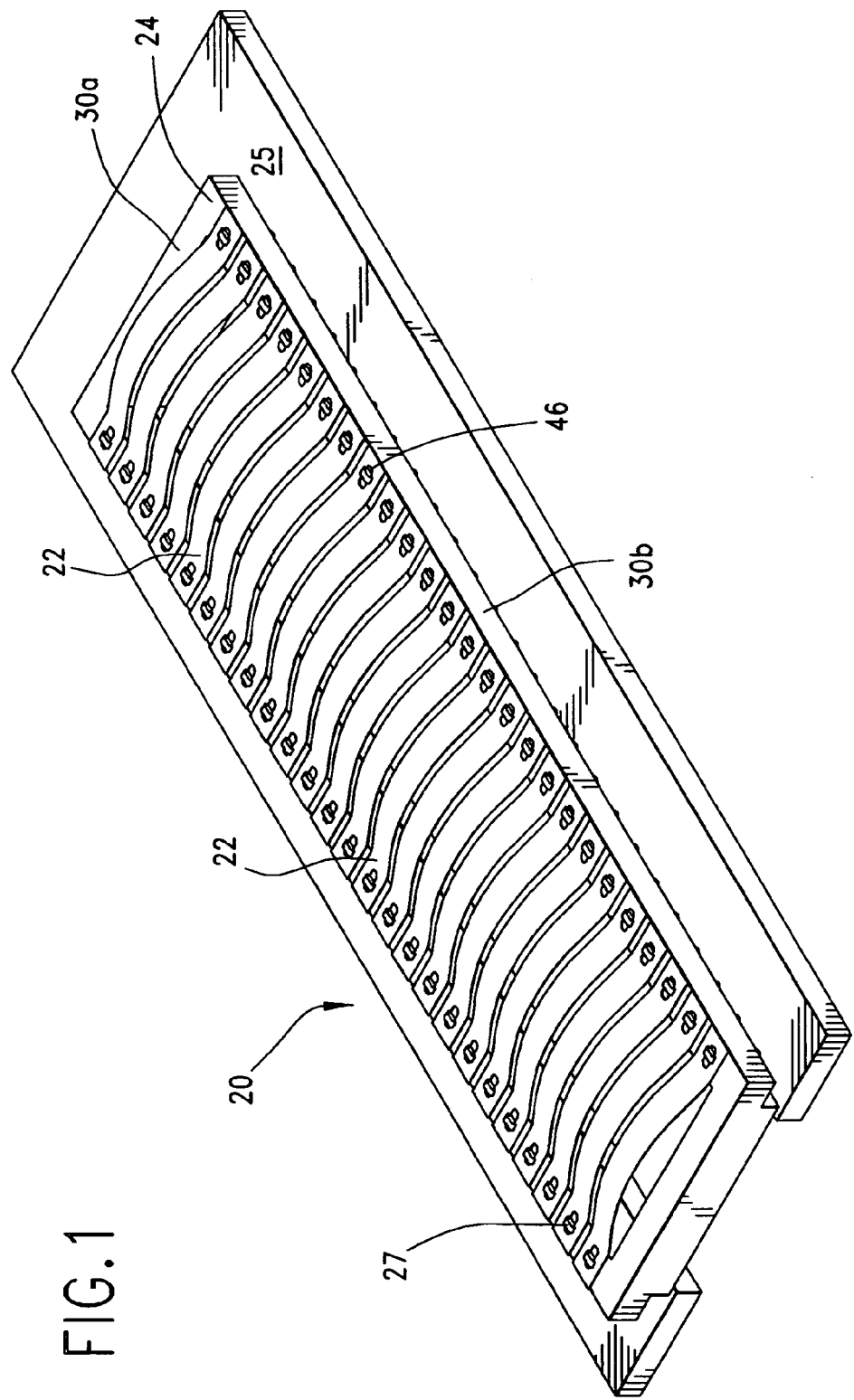
FIG. 1 is a perspective view of a heating element connector assembly constructed in accordance with the principles of the present invention, shown in position as mounted to a printed circuit board.

FIG. 1 illustrates a heating element connector assembly 20 that is constructed in accordance with the principles of the present invention. The assembly 20 is comprised of a plurality of individual conductive strips 22 that are supported by a frame 24, which is mounted to a circuit board 25. The individual strips are preferably formed from a conductive material such as a metal foil, or the like.

Figure 2:
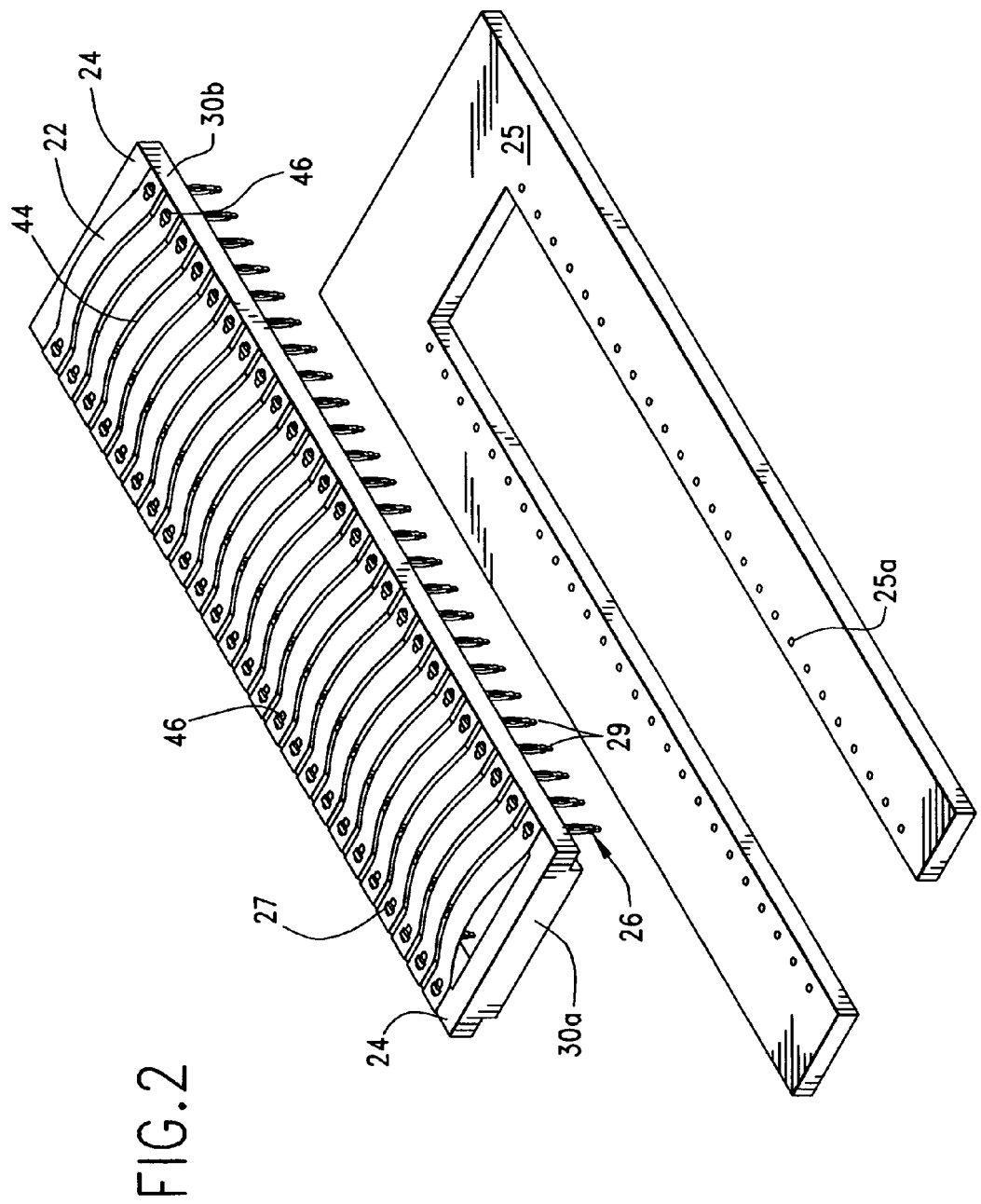
FIG. 2 is the same view as FIG. 1, but with the heating element assembly removed from its connection to the printed circuit board.

The strips 22 each define an individual heating element of the assembly, which can be heated when a current is passed through the strip 22. In this regard, the strips 22 are supported by an insulative frame 24, and the frame 24 contains a plurality of conductive terminals 26, as illustrated in FIG. 2 for example. Each terminal 26, as explained in greater detail to follow, has a contact portion 27 that makes contact with the strips 22, and a tail portion 29 that extends out from the frame 24 and which provides a means of connecting the individual strips 22 to heating circuits on the circuit board 25 which provide a pass through current to energize the strips 22. The terminal tail portions 29 are preferably received within plated through holes 25a formed in the circuit board 25.

Figure 3:
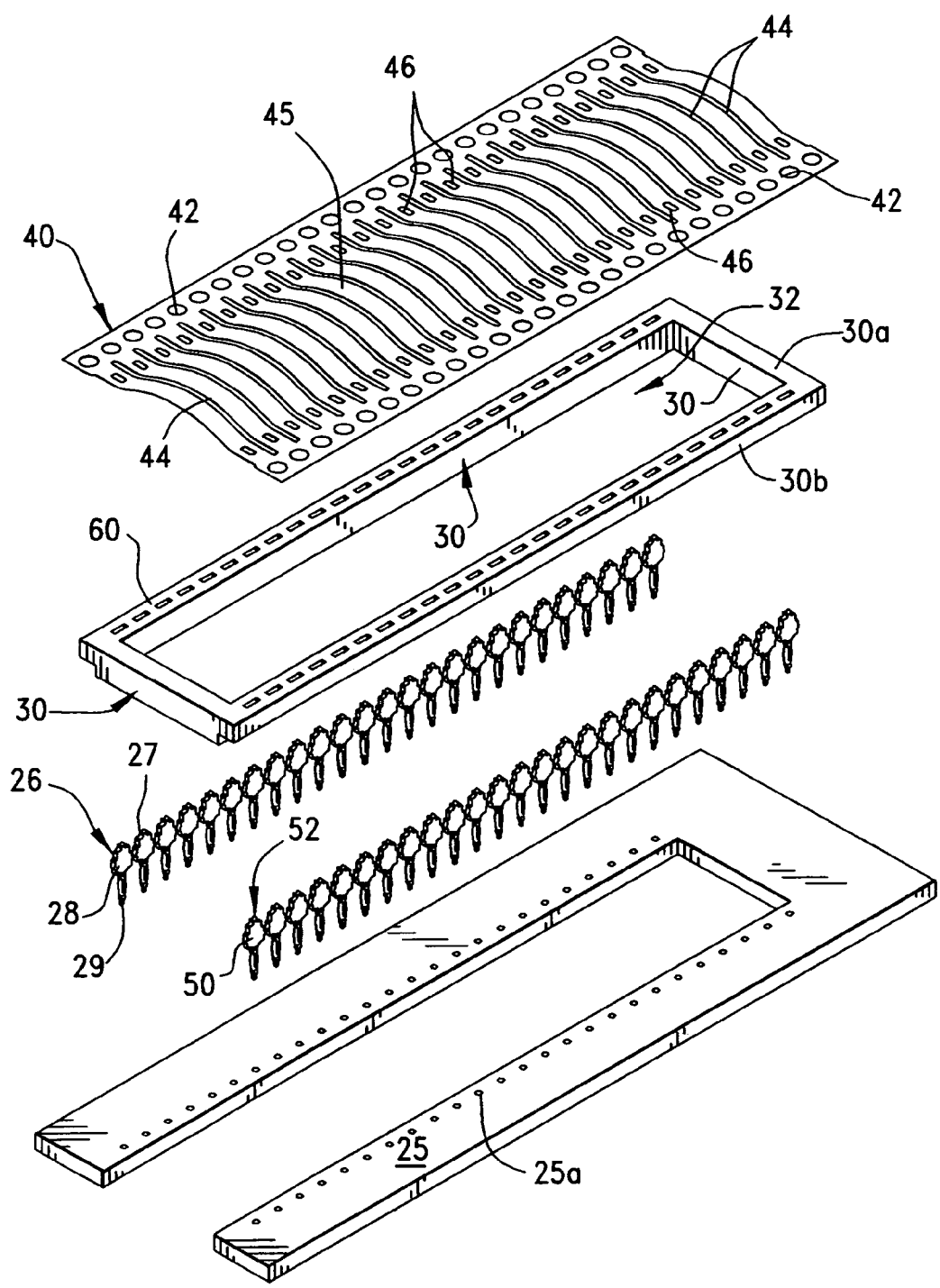
FIG. 3 is an exploded view of the heating element assembly of FIG. 1.
Figure 4:
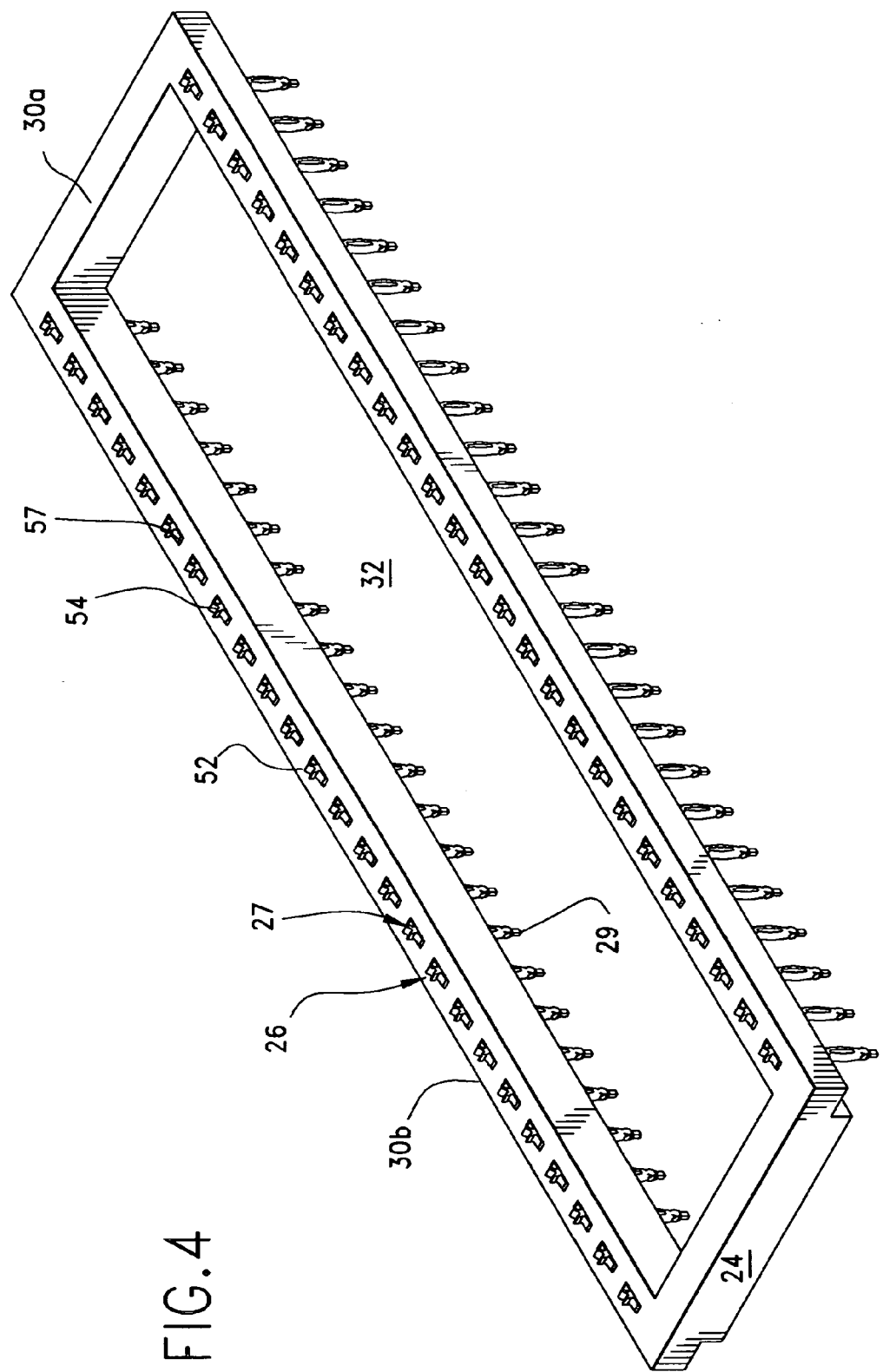
FIG. 4 is a perspective view of the heating element frame with the conductive strips removed for clarity.
Figure 5:
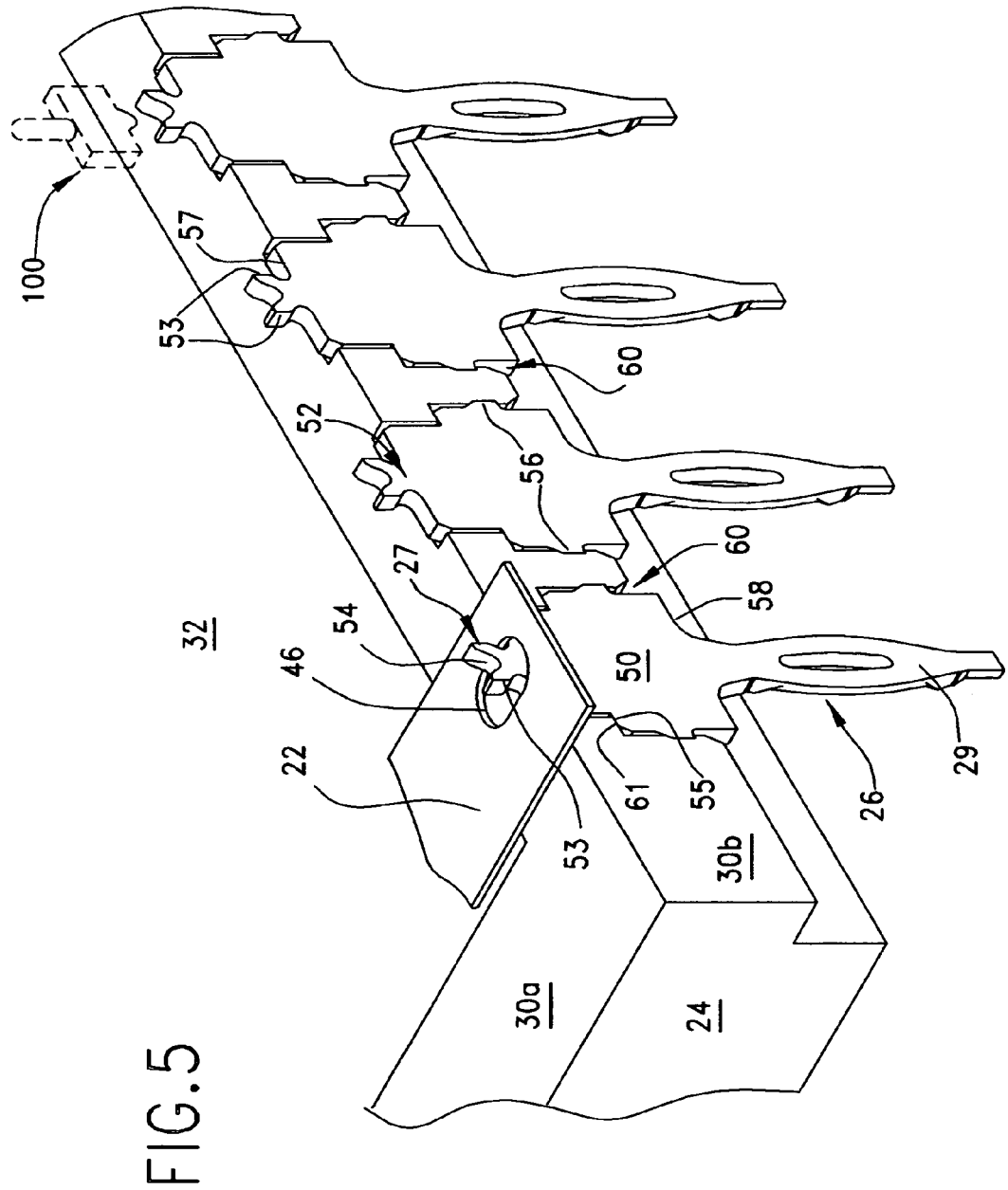
FIG. 5 is an enlarged detail view of one of the sides of the frame, shown partially in section, illustrating the placement of the terminals within the frame.

FIG. 3 illustrates the assembly 20 in exploded fashion, while FIG. 5 illustrates the terminals in greater detail. As shown, the frame 24 is rectangular in shape having four sidewalls 30 that cooperatively define a central opening 32. The frame sidewalls 30 include end walls 30a and longitudinal sidewalls 30b which in most instances will have a length longer than that of the end walls 30a in order to give the assembly its rectangular configuration shown. The sidewalls 30b are spaced apart from each other and the opening 32 is spanned by the conductive strips 22.

Figure 7:
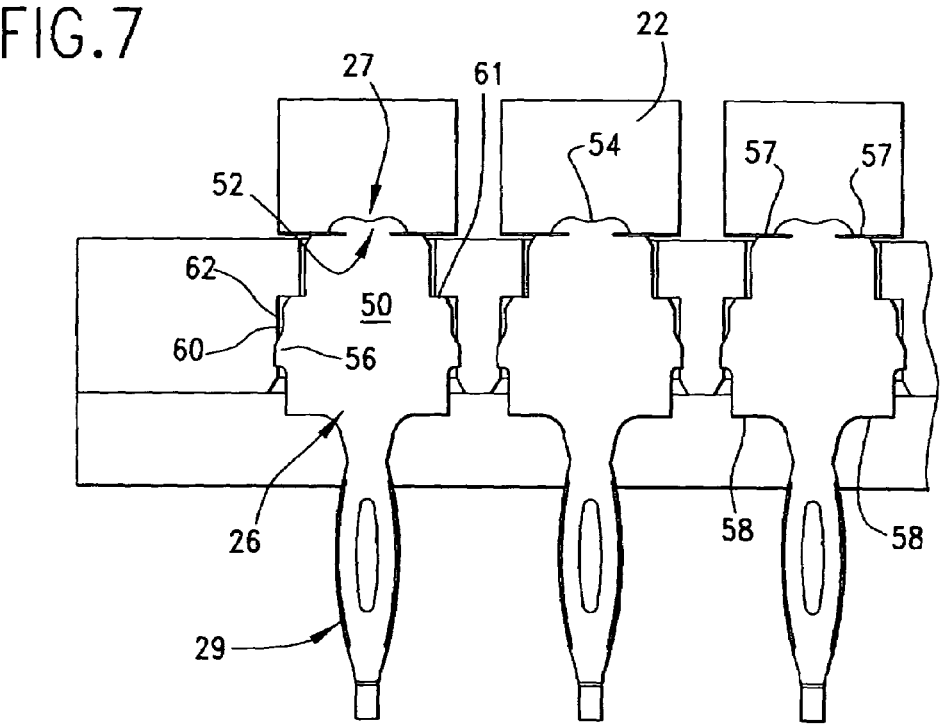
FIG. 7 is a side elevational view of a portion of FIG. 5, illustrating the contact portions of the terminals in a flattened state and connecting the conductive strips to the terminals; and, FIG. 8 is a enlarged detail perspective view of one end of the heating element connector of FIG. 1, illustrating the manner in which the terminals are connected to the conductive strips.

The strips 22 are formed as part of an overall carrier strip or assembly 40 that is also configured to match the configuration of the frame 24 and which is shown as rectangular in the drawings. The carrier strip 40 has advancement and registration openings 42 formed along opposing longitudinal edges thereof and it also has a series of transverse slots 44 that are shown as positioned between the edge openings 42. These slots 44 serve to define the body portions 45 of the strips 22. The ends of the body portions 45 of the strips contain attachment holes 46 which will receive the contact portion of a terminal therein The terminals 26 further have wide body portion 50 as shown. The terminal contact portions 27 can be see in FIG. 5 to rise up from the terminal body portions 50. The contact portions are best described as deformable lugs 52, and to facilitate their deforming, the lugs may include a pair of arm portions 53 that extend on opposite sides of a center notch 54. With this center notch 54, a deforming tool 100 (shown in phantom in FIG. 5) in the form of a center punch or the like may be used to contact the lug 52 and deform it so that the lug 52 preferably deforms within the plane of the terminal body portion. In this manner, the lug arm portions 53 will extend sideways of the terminal and preferably in the plane of the terminal body portion 50 and flatten out, as shown best in FIG. 7 to crimp, or press, against the conductive strips 22. The center notch 54 may be slightly curved as shown so that the resulting flattened contact lug (or "deadhead") may have a curved shape with out any sharp breaks that may cause areas of high stress which might negatively affect the connection.

The terminals 26 are received in terminal-receiving cavities 60 that are best shown in FIG. 5, and which can be seen to include inner steps 61 that are formed therein. These steps 61 act as stop surfaces and engage the corresponding shoulders 55 that are formed on the terminal body portions 50. These shoulders 55 extend outwardly sideways from the body portions 50. The terminals 26 may also include skiving portions 56 that cut into the sidewalls 62 of the cavities 60.

The terminal body portions 50 also can be seen to include opposing flat ends 57, 58. The bottom ends form first reaction surfaces 58 against which a tool (not shown) may press in order to insert the terminals 26 into their terminal-receiving cavities 60. The top flat ends 57 of the terminals 26 likewise form second reaction surfaces against which the aforementioned punch 100 may deform the contact lugs 52. These second reaction surfaces may bear against a surface in a loading device or jig and serve as a second stop surface that limits the extent to which the terminals 26 may be inserted into their associated cavities 60.

Figure 6:
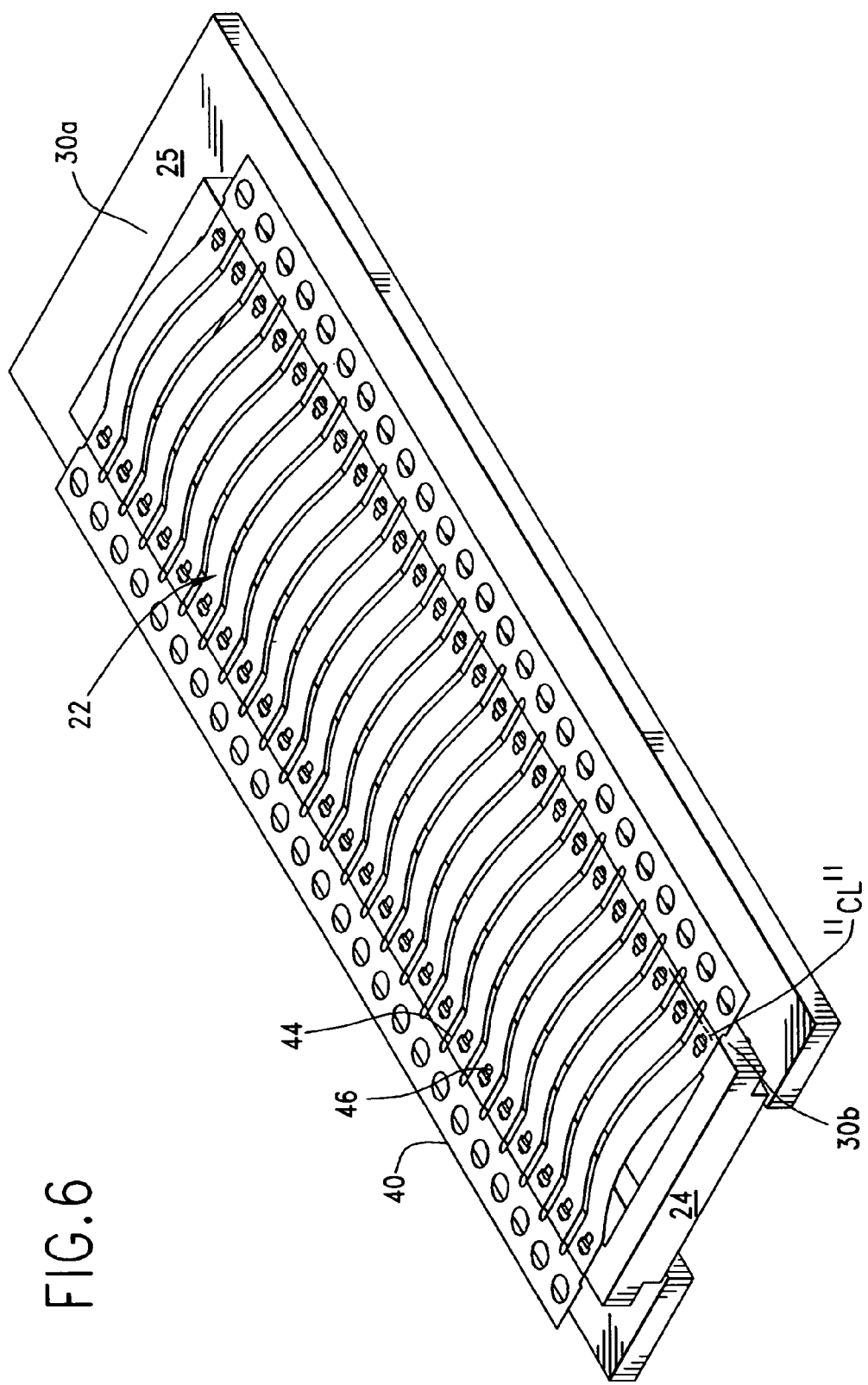
FIG. 6 is the same view as FIG. 4, but with a carrier strip of conductive strips positioned in place thereon, prior to singulation of the strips.
Figure 8:
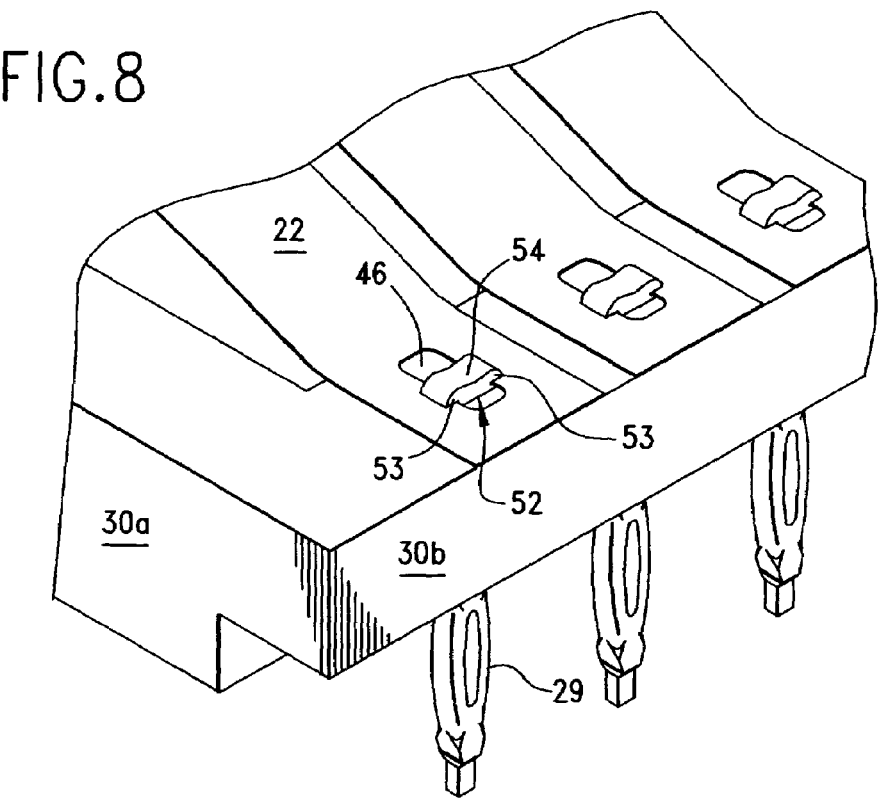

The conductive strips preferably have a length that is greater than the distance separating the frame sidewalls 30b so that the center portions of the strips 22 are crowned, or rise above or are spaced away from the top surfaces of the frame 24 as shown in the Figures. The attachment openings 46 of the strips 22 may be as shown in drawings, openings that run lengthwise of the strips 22 so that the deformable lugs 52 of the terminals 26 will deform in a direction perpendicular to the extent of the openings 46. This is shown best in FIG. 8. As shown in FIG. 6, the carrier strip 40 may be assembled over a frame 24 filled with terminals 26 and then after the terminal contact portions 27 have been deformed, the carrier strip may be cut or singulated along a cut line "CL" to form an array of individual conductive strips 22 that are connected to the terminals 26.

While the preferred embodiment of the invention have been shown and described, it will be apparent to those skilled in the art that changes and modifications may be made therein, including combinations of the various features described herein, without departing from the spirit of the invention, the scope of which is defined by the appended claims.

The invention claimed is:

1. An improved connector assembly, the assembly comprising:

an insulative frame, the frame including a pair of lengthwise side walls that are interconnected together by widthwise end walls, the side walls and end walls cooperatively defining a central opening of the frame;

a plurality of conductive terminals supported by said frame, the terminals being spaced apart from each other in an array that runs lengthwise in each of said two sidewalls, said terminals being aligned with each other in pairs in said two sidewalls across the frame opening, each of said terminals including tail and contact portions disposed at opposite ends thereof, the terminal tail portions including compliant pin tail portions for receipt by corresponding holes in a circuit board and the terminal contact portions including deformable lugs extending upwardly above a level of said frame sidewalls; and, a plurality of conductive strips extending across the frame opening and interconnecting pairs of terminals together.

2. The connector assembly of claim 1, wherein said conductive strips are formed from a conductive foil and exhibit a crown with respect to said frame side walls, said crown being defined by said conductive strips being spaced away from said frame side walls.

3. The connector assembly of claim 1, wherein said conductive strips comprise heating elements that have current-responsive properties and that elevate in temperature when electric current is passed therethrough.

4. The connector assembly of claim 1, wherein said tail portions of the conductive terminals are sized and shaped for reception within conductive holes of a circuit board.

5. The connector assembly of claim 1, wherein each of said conductive terminals includes a body portion interconnecting said tail and contact portions together.

6. The connector assembly of claim 5, wherein said body portion has a width that is greater than the width of said tail of that conductive terminal and greater than the width of said contact portion of that conductive terminal.

7. The connector assembly of claim 5, wherein said frame includes a plurality of terminal-receiving cavities, each of said terminals being received within a single one of the terminal-receiving cavities, each of said terminal-receiving cavities includes at least one stop surface, and said terminal body portions include a least one shoulder portion that bears against said terminal-receiving cavity stop surface.

8. The connector assembly of claim 1, wherein each of said terminal contact portion deformable lugs includes a center notch for spreading said lugs outwardly when the lug is deformed.

9. The connector assembly of claim 8, wherein said terminal body portions each include a pair of flat surfaces flanking said contact portion, the flat surfaces defining reaction surfaces against which said deformable lug may be deformed.

10. The connector assembly of claim 8, wherein said deformable lug includes a pair of contact arms that are separated by said center notch, the contact arms being deformed into contact with said conductive strips.

11. The connector assembly of claim 10, wherein the contact arms that are deformed into contact with the conductive strips define the deformable lugs as flattened contact lugs having a curved shape devoid of sharp breaks.

12. The connector assembly of claim 10, wherein said conductive strips include attachment openings that extend lengthwise of said conductive strips, and said contact arms extend perpendicularly to the attachment openings.

13. An improved connector assembly, the assembly comprising:

an insulative, rectangular frame, the frame including a pair of lengthwise side walls that are interconnected together by widthwise end walls, the side walls and end walls cooperatively defining a central opening of the frame;

a plurality of conductive terminals supported by said frame, the terminals being spaced apart from each other in an array that runs lengthwise in each of said two sidewalls, said terminals being aligned with each other in pairs in said two sidewalls across the frame opening, each of said terminals including a body portion interconnecting tail and contact portions disposed at opposite ends of the body portion, the body portion being wider than either of the tail portion or the contact portion, the terminal tail portions including compliant pin tail portions for receipt by corresponding holes in a circuit board and the terminal contact portions including deformable lugs extending upwardly above a level of said frame sidewalls, the terminal contact portion deformable lugs including a center notch between said lugs; and, a plurality of conductive strips extending across the frame opening and interconnecting pairs of terminals together.

14. The connector assembly of claim 13, wherein said conductive strips are formed from a conductive foil and exhibit a crown with respect to said frame side walls, said crown being defined by said conductive strips being spaced away from said frame side walls.

15. The connector assembly of claim 13, wherein said conductive strips comprise heating elements that have current-responsive properties and that elevate in temperature when electric current is passed therethrough.

16. The connector assembly of claim 13, wherein said tail portions of the conductive terminals are sized and shaped for reception within conductive holes of a circuit board.

17. The connector assembly of claim 13, wherein said frame includes a plurality of terminal-receiving cavities, each of said terminals being received within a single one of the terminal-receiving cavities, each of said terminal-receiving cavities includes at least one stop surface, and said terminal body portions include a least one shoulder portion that bears against said terminal-receiving cavity stop surface.

18. The connector assembly of claim 17, wherein said terminal body portions each include a pair of flat surfaces flanking said contact portion, the flat surfaces defining reaction surfaces against which said deformable lug may be deformed.

19. The connector assembly of claim 13, wherein said deformable lug includes a pair of contact arms that are separated by said center notch, the contact arms being deformed into contact with said conductive strips.

20. The connector assembly of claim 19, wherein the contact arms that are deformed into contact with the conductive strips define the deformable lugs as flattened contact lugs having a curved shape devoid of sharp breaks.

21. The connector assembly of claim 19, wherein said conductive strips include attachment openings that extend lengthwise of said conductive strips, and said contact arms extend perpendicularly to the attachment openings.

* * * * *